(12) United States Patent
Abou Khousa et al.

(10) Patent No.: US 9,970,804 B2
(45) Date of Patent: May 15, 2018

(54) METHOD AND APPARATUS TO DETECT CONTAMINANTS IN PRESSURIZED FLUID FLOWS

(71) Applicant: Emirates Innovations, London (CA)

(72) Inventors: Mohamed Abou Khousa, Al-Ain (AE); Ahmed Al-Durra, Al-Ain (AE); Khaled Mohamed Abdulla Mohsen Alwahedi, Abu Dhabi (AE)

(73) Assignee: Emirates Innovations, Ontario (CA)

( * ) Notice: Subject to any disclaimer, the term of this patent is extended or adjusted under 35 U.S.C. 154(b) by 310 days.

(21) Appl. No.: 14/828,966

(22) Filed: Aug. 18, 2015

(65) Prior Publication Data

US 2016/0054161 A1    Feb. 25, 2016

Related U.S. Application Data

(60) Provisional application No. 62/039,258, filed on Aug. 19, 2014.

(51) Int. Cl.
| | | |
|---|---|---|
| *G01F 1/00* | (2006.01) | |
| *G01F 1/74* | (2006.01) | |
| *G01F 1/66* | (2006.01) | |
| *G01F 1/708* | (2006.01) | |
| *G01N 22/00* | (2006.01) | |
| *G01N 15/06* | (2006.01) | |

(Continued)

(52) U.S. Cl.
CPC .................. *G01F 1/74* (2013.01); *G01F 1/66* (2013.01); *G01F 1/708* (2013.01); *G01N 15/06* (2013.01); *G01N 22/00* (2013.01); *G01N 33/225* (2013.01); *G01N 2015/0046* (2013.01); *G01N 2015/0687* (2013.01)

(58) Field of Classification Search
CPC .. G01F 1/74; G01F 1/66; G01F 1/708; G01N 2015/0046; G01N 2015/0687; G01N 33/225
See application file for complete search history.

(56) References Cited

U.S. PATENT DOCUMENTS 3,498,112 A    3/1970    Howard
3,939,406 A    2/1976    Billeter et al.
(Continued)

FOREIGN PATENT DOCUMENTS

EP    0703447 A2    3/1996
EP    2500699 A1    9/2012

OTHER PUBLICATIONS

Abou-Khousa, Mohamed A. et al., Hermetically Sealed Microwave Probe for in-situ Detection of Black Powder in Gas Pipelines, Instrumentation and Measurement Technology Conference (I2MTC) Proceedings, 2014 IEEE International, May 12-15, 2014, pp. 1115-1119.

(Continued)

*Primary Examiner* — Matthew G Marini
(74) *Attorney, Agent, or Firm* — Senniger Powers LLP

(57) ABSTRACT

Method and apparatus for the detection and measurement of contaminant concentration within pressurized fluid flows in real-time. The provided method and apparatus allow for real-time detection of black powder contaminants in pressurized gas flows by irradiating the flow with electromagnetic waves generated by hermetically-sealed electromagnetic wave radiators and measuring wave characteristics. An image is rendered of the spatial distribution of black powder within the pipe cross section, and mass flow of the contaminated gas is measured.

20 Claims, 12 Drawing Sheets

(51) Int. Cl.
  *G01N 15/00*  (2006.01)
  *G01N 33/22*  (2006.01)

(56) References Cited

U.S. PATENT DOCUMENTS

| | | |
|---|---|---|
| 4,289,020 A | 9/1981 | Paap |
| 4,820,970 A | 4/1989 | Swanson |
| 4,902,961 A | 2/1990 | De et al. |
| 4,996,490 A | 2/1991 | Scott et al. |
| 5,001,434 A | 3/1991 | Marrelli et al. |
| 5,014,010 A | 5/1991 | Helms et al. |
| 5,101,163 A | 3/1992 | Agar |
| 5,150,061 A | 9/1992 | Castel et al. |
| 5,351,521 A | 10/1994 | Cracknell |
| 5,369,368 A | 11/1994 | Kassen et al. |
| 5,389,883 A | 2/1995 | Harper |
| 5,412,326 A | 5/1995 | Marrelli et al. |
| 5,625,293 A | 4/1997 | Marrelli et al. |
| 5,793,216 A | 4/1998 | Constant |
| 5,864,240 A | 1/1999 | Hirai et al. |
| 6,826,964 B2 | 12/2004 | Nyfors |
| 7,587,290 B2 | 9/2009 | Scott |
| 7,770,469 B2 | 8/2010 | Nyfors et al. |
| 7,908,930 B2 | 3/2011 | Xie et al. |
| 8,109,161 B2 | 2/2012 | Jovancicevic et al. |
| 8,285,491 B2 | 10/2012 | Xie et al. |
| 8,322,228 B2 | 12/2012 | Xie et al. |
| 2009/0107252 A1 | 4/2009 | Okazaki |
| 2011/0283809 A1 | 11/2011 | Pihlaja et al. |
| 2014/0125516 A1 | 5/2014 | Ghasr et al. |

OTHER PUBLICATIONS

Abou-Khousa, Mohamed et al., Microwave Sensing System for Real-Time Monitoring of Solid Contaminants in Gas Flows, Sensors Journal, IEEE, Jun. 3, 2015, vol. 15, Issue 9, pp. 5296-5302.
International Search Report dated Nov. 3, 2015 relating to PCT Application No. PCT/IB2015/056285, 5 pages.
Written Opinion dated Nov. 3, 2015 relating to PCT Application No. PCT/IB2015/056285, 6 pages.
Extended European Search Report for application No. EP15833323.7, dated Mar. 22, 2018, 6 pages.

METHOD AND APPARATUS TO DETECT CONTAMINANTS IN PRESSURIZED FLUID FLOWS

CROSS REFERENCE TO RELATED APPLICATION

This application the non-provisional application of U.S. Provisional Application Ser. No. 62/039,258 entitled Method and Apparatus to Detect Contaminants in Pressurized Fluid Flows, filed on Sep. 5, 2014, the contents of which are incorporated herein by reference in their entirety for all purposes.

BACKGROUND

Aspects of the present invention generally relate to the detection of undesired contaminants in fluid flows within structures such as pipelines and vessels, using electromagnetic waves. More specifically, aspects of the present invention relate to the real-time detection and monitoring of black powder contaminants within gas flows in natural gas pipelines. Conventional systems for detecting undesired contaminants generally function by transmitting and receiving an electromagnetic signal through a multiphase flow, and inferring the dielectric properties of the flow based on the amplitude and phase change of the received signal. Such detectors also function by deducing flow properties based on the shift of the resonance frequency as well as the quality factor in the transmitted signal.

Pipelines and vessels are typically made out of either metallic materials (e.g., steel) or non-metallic materials (e.g., plastics and composites). Such structures are used extensively for fluid transmission in many industries including the oil and gas industry. When used for natural gas transmission, steel pipelines are susceptible to undesired solid contaminants in the form of black powder carried within the gas flow. Black powder is a general term used to describe dry or wet fine powder material, e.g., solid particles, consisting of various corrosion products such as iron oxides, iron sulfides, and other contaminants such as dirt and sand. Black powder is a recognized threat to the integrity and operation of transmission pipelines in many different regions around the world.

Although the formation mechanism of black powder can vary, those skilled in the art believe that the initiation of black powder can be attributed at least in part to the hydrotesting phase during the pipeline commissioning stage. Regardless of how it originates, black powder adversely impacts the integrity of gas pipelines and the controls and instrumentation associated with the pipelines, which may lead to partial or even complete shutdown and lost production. For example, black powder accumulation causes valve damage, compressor failure, and instrumentation clogging leading to expensive repairs. In many instances, black powder contaminants propagate further to downstream processes and utility companies. In addition to potential physical asset damage, the propagation of the contaminants raises critical quality-of-service complaints and flow assurance concerns which may reflect negatively upon the image of the supplier.

Black powder is currently only discoverable through examining the consequences of its presence in a given pipeline section, such as by end-user complaints, or by discovering the indications of black powder residuals by inspecting components such as a failed compressor, a clogged flow meter, or a due-for-replacement line filter. After detecting black powder in a particular pipeline, it is typically managed, i.e., removed from the victim line, through routine pipeline maintenance procedures using various well-established methods such as filtration, gel-based or surface active agents-based cleaning and aggressive pigging. This, however, does not solve the problem completely because the discovered black powder in the cleaned line might have originated from a different pipeline in the network and transported with the flow to the victim line. Due to the lack of effective black powder detection methods, the source of the black powder is rarely discovered and hence not treated. Consequently, the problem soon arises again and repairs on the victim lines must be repeated.

The black powder flow in a gas pipeline is a two-phase (solid-gas) dielectric mixture. The presence of black-powder in the pipeline changes the effective medium in the pipe cross section. There is no doubt that the black powder particles have physical and chemical properties that are distinct from the host gas carrying the black powder. Such chemical or physical contrasts can be the basis for many detection methods. In principle, the contrast in the magnetic, electrical, electromagnetic, optical, thermal, and mechanical properties between the black powder and its host gas can be exploited to develop viable detection techniques. For instance, differential weight measurements have been used to measure black powder deposits in gas pipelines. Unfortunately, this method is not applicable for detecting the black powder in motion with the gas flow as desired in many applications. Ultraviolet and visual spectrometers have also been used to detect liquids in gas flows.

Previously, microwave measurement techniques for multiphase mixture characterization and liquid flow metering have been employed in many multiphase metering technologies and liquid flow sensors, alone as well as combined with other methods such as gamma rays. Although microwave techniques are particularly promising for multi-phase component fraction measurements, current solutions are lacking.

In general, determining multiphase component fractions using microwave methods is founded on the electromagnetic interaction between the electromagnetic waves and the dielectric medium in the pipe. Conventional methods of deducing the dielectric properties of the multiphase mixture at microwave frequencies are generally based on two approaches. In the first approach, the dielectric properties, i.e. permittivity, of the multiphase flow are inferred from amplitude and phase change of a microwave signal passing through the flow or reflected from the flow. In the second approach, these properties are deduced from the shift of the resonance frequency and change in the quality factor of a microwave resonant cavity containing the multiphase flow.

These conventional techniques have several shortcomings. For example, they cannot be applied to detect black powder within pressurized natural gas flows. In particular, the techniques do not address the significant problem of coping with high pressure applications. Furthermore, they either use the pipeline as a waveguide cavity resonator, or they are based on resonant inserts placed in the flow, which tend to perturb the process flow and decrease measurement accuracy. Also, most of these methods are limited to metallic pipelines.

Additionally, many techniques predict the flow properties from either detecting a shift in the resonance frequency, Doppler frequency shift, and/or detecting the attenuation of the microwave signal between two measurement points along flow direction. But these techniques have not been demonstrated as capable of detecting very small black powder flow rates, such as rates at less than 1 g/s typically encountered in practice

SUMMARY

Briefly, aspects of the present invention permit detecting black powder inside gas pipeline networks in real time. As is understood by those skilled in the art, black powder should be detected as early as possible and its source should be localized and treated to avoid severe black powder consequences and to design cost-effective pipeline maintenance protocols. Aspects of the invention permit early detection of black powder in susceptible lines for efficient pipeline management and "Best in Class" maintenance. In this regard, aspects of the present invention provide a sensitive detection device that allows in-field evaluation of the installed filters to detect the presence of black powder and measure its concentration within the flow in its early stages. This not only enables cost-effective maintenance procedures but also allows for tracing the initiating source of the black powder, fully understanding its formation mechanism, and eliminating the problem completely from the origin. Moreover, aspects of the present invention embody improvements that permit black powder detection without requiring use of cavity resonators or resonator inserts and without requiring use of the pipeline as a waveguide for the microwaves. In this regard, detection is permitted in both metallic and non-metallic pipelines at an improved level of sensitivity, without involving any type of sampling for the gas-black-powder mixture. Aspects of the invention provide detection of very small black powder flow rates (less than 1 g/s) even under high temperature, high pressure, and/or high flow rate conditions.

In an aspect, an apparatus characterizes multiphase flow in a pipe transporting a fluid under pressure. The apparatus includes a transmitter to generate a signal. A first antenna transmits the signal through a first transmission line to a fluid contained within a section of pipe, and is also configured for receiving a reflected portion of the signal. A second antenna receives a portion of the signal "transmitted through" the fluid. A first diode detector detects a standing wave in the first transmission line, the standing wave comprising the reflected portion of the transmitted signal and the original transmitted signal, producing a first voltage representing the standing wave. A second diode detector produces a second voltage based on the transmitted through signal received by the detector from the second antenna. A preamplifier/filter, a converter, and a monitoring processor further process the first and second voltages to identify characteristics of the flow.

In another aspect, a method for detecting components within a pressurized gas flow mixture is provided.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Aspects of the present invention relate to detection of undesired contaminants, namely, black powder. More specifically, improved methods and systems involving black powder detection are described. The presence of black powder in the pipeline changes the effective dielectric medium of the flow in the line. The dielectric properties (i.e., complex permittivity and permeability) of the black powder are significantly different than the host gas flow. Hence, the presence of the black powder, even in small concentrations, changes the effective dielectric properties of the flow considerably. Microwaves are sensitive to minute dielectric variations. Specifically, these waves undergo scattering (reflection) and attenuation as they impinge and pass through the cross section of the pipeline containing black powder. Two main embodiments that utilize this interaction are described in the following.

1. Microwave Detection Apparatus and Method

Figure 1:
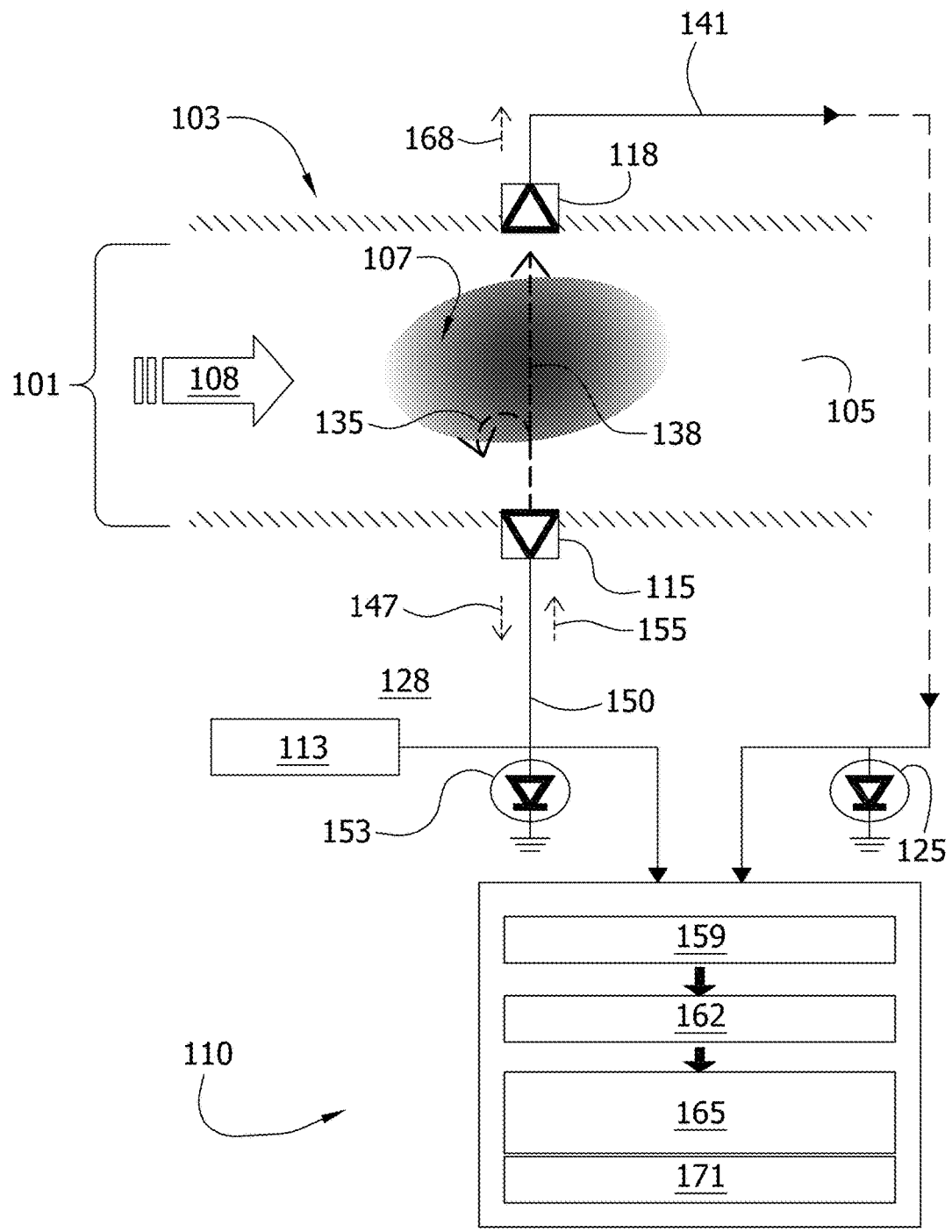
FIG. 1 depicts a microwave detection apparatus in accordance with one embodiment of the invention.

FIG. 1 depicts a microwave detection apparatus in accordance with one embodiment of the invention. As depicted by FIG. 1, a pipeline 101, which has a pipe wall 103, carries a mixture of gas 105 and contaminants 107 within a flow 108 of process fluid. For instance, the contaminants 107 include black powder. Additionally, FIG. 1 depicts a detection apparatus 110 according to a preferred embodiment. As depicted in FIG. 1, the apparatus 110 includes, among other components, a transmitter 113, a transmitting antenna 115, a receiving antenna 118, a first transmission line 141, a second transmission line 150, a first diode detector 125, and a second diode detector 153. In an embodiment, the detection apparatus 110 of FIG. 1 is hermetically-sealed for use in fluid environments. The transmitter 113 generates a microwave signal 128 carried by the second transmission line 150 to the transmitting antenna 115 as transmitted signal 155. The transmitting antenna 115 in turn launches the supplied microwave signal 128 (i.e., transmitted signal 155) through the pipe wall 103 into the flow 108 inside the pipeline 101.

When microwaves impinge upon the gas 105 component of the flow 108 that carries black powder contaminants 107, a portion of the incident wave reflects back towards the transmitting antenna 115 as a reflected wave 135. The remaining wave portion passes through the flow 108 as a transmitted-through wave 138. The transmitted-through wave 138 is picked up at the receiving antenna 118, which is on the pipe wall 103 on the other side of pipeline 101. The receiving antenna 118 delivers a signal 168 representative of transmitted-through wave 138 via a first transmission 141 line to a first diode detector 125. The first diode detector 125 produces a voltage proportional to the power in the transmitted-through signal 168 ($V_T$) at node 144. Also, the reflected wave 135 is picked up by the transmitting antenna 115 and propagates as a reflected signal 147 in a second transmission line 150 where it is superimposed on the opposite-traveling transmitted signal 155 creating a standing wave. The power in the formed standing wave is detected using a second diode detector 153 that produces a voltage proportional to this power (Vs) at node 156. In the illustrated embodiment, a Pre-Amplifier/Filter 159 filters and amplifies the detected voltages before they are sampled using analog to digital converter 162. A Processing Unit/Display 165, which comprises a microprocessor, personal computer, or the like, processes and displays the digitized voltages. The Pre-Amplifier/Filter 159, the analog to digital converter 162, and the Processing Unit/Display 165 are powered by a power supply 171.

The presence of the black powder contaminants 107 within the flow 108 alters the phase angle and amplitude (power) of the complex reflected signal 147 and transmitted-through signal 168 in a specific way that is correlated to the concentration of the black powder contaminants 107 within the gas 105 that comprises the flow 108.

Figure 2:
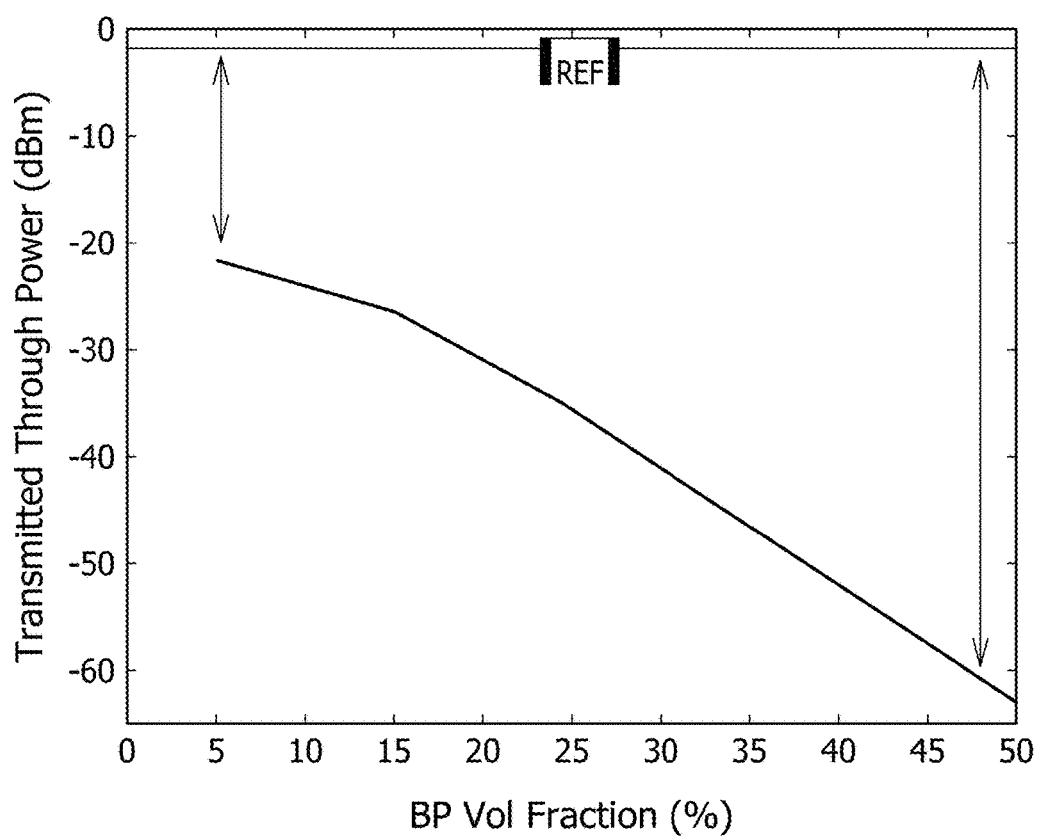
FIG. 2 is an exemplary graph depicting dependency of the transmitted-through signal power on the volume fraction of black powder in a 3-inch pipe.

For instance, FIG. 2 illustrates the dependency of the power of a transmitted-through signal (proportional to $V_T$) on the volume fraction of black-powder at 24 GHz in a 3-inch pipeline ("no-black-powder" case is set at 0 dBm as reference). As shown in FIG. 2, besides the induced change due to the presence of black powder (20 dB for 5% volume fraction), there is a one-to-one relation between the power of the transmitted through signal (in dB) with the black powder concentration. In this example, the detection dynamic range is 42 dB. Although, in this particular example, measuring the power of the transmitted through signal could be relied upon for detection and quantification, measuring more parameters as provided by the system shown in FIG. 1 (two measurements: $V_T$ and $V_S$) provides diversity to compact non-unique mappings that might arise in larger pipes, decrease the measurement uncertainties, and enhance the detection dynamic range.

Based on the apparatus 110 shown in FIG. 1, a microwave detection device working at 24 GHz was realized using simple power detectors. To launch/receive the microwave signal into/from the pipe, a compact hermetically-sealed antenna that is properly coupled to the pipe was designed. The designed antenna is non-perturbing to the flow and isolated from it. Furthermore, the antenna construction and its coupling mechanism can withstand the pressure encountered typically in practice. As desired, the antenna uses a standard coupling mechanism such as tap holes and thread-o-lets similar to most standard sensors which are typically interfaced to the pipe based on such coupling. Since the antenna is configured with standard coupling, the apparatus 110 can be installed on spare pre-tapped locations typically found in the network for flow sampling and instrumentation purposes.

Figure 3A:
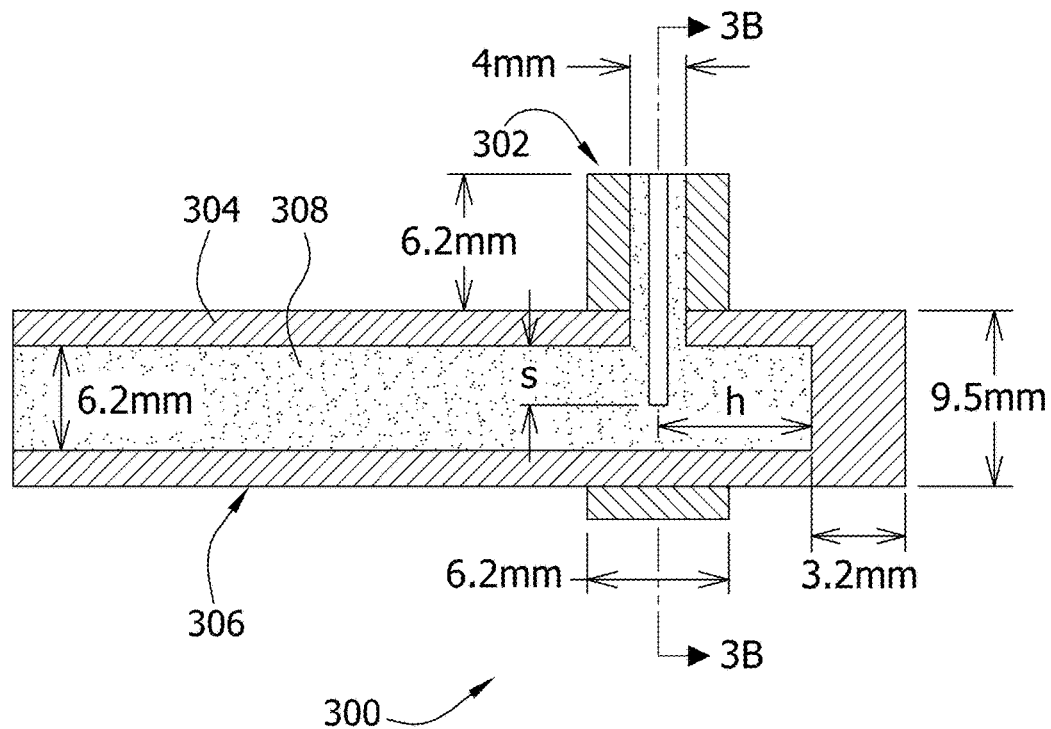
FIG. 3(a) is a cross-sectional side view of an antenna constructed in accordance with one embodiment of the invention.
Figure 3B:
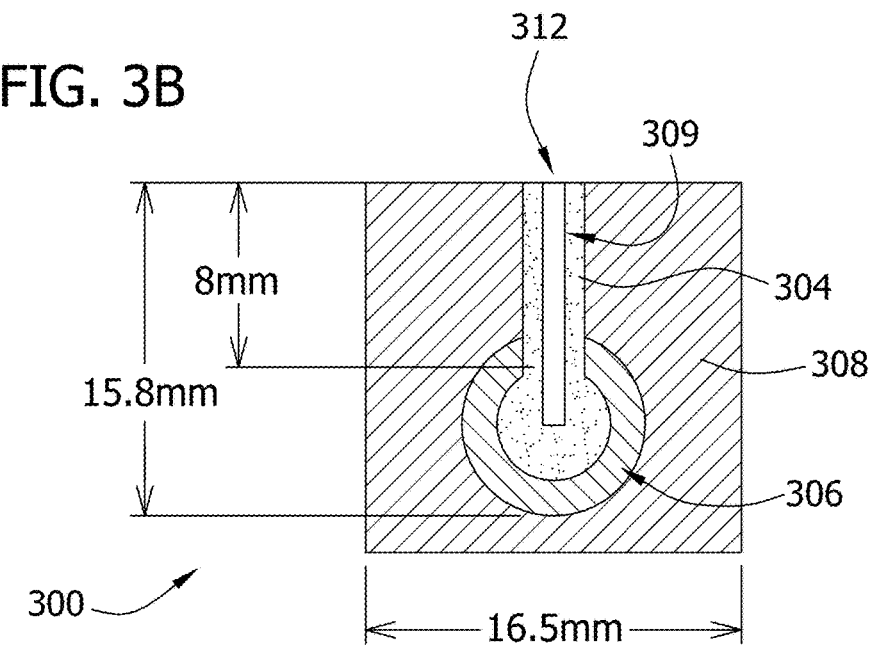
FIG. 3(b) is a cross-sectional end view of the antenna of FIG. 3(a).

FIGS. 3(a) and 3(b) depict longitudinal and cross-sectional dimensions of an antenna (e.g., antenna 115 or antenna 118) constructed in accordance with one embodiment of the invention. To construct an antenna according to an embodiment with attributes that provide for the detection of black powder contaminants 107 as described above, a probe 300 comprising a circular waveguide as shown in FIGS. 3(a) and 3(b) is disclosed. In an embodiment, the circular waveguide works in the $TE_{11}$ mode region and is fed through TEM-to-$TE_{11}$ transition by a 50 ohm coaxial line. In another embodiment, the disclosed antenna is constructed by using a single block 304 of "type 303 stainless steel" or the like to machine both the transition (feed) section 302 as well as the circular waveguide 306 section from the same block of steel (cf. FIG. 3(a) for dimensions) without creating weak joints.

In an embodiment, a rod 308 comprised of a fluorocarbon solid or the like (e.g., TEFLON® polytetrafluoroethylene) is press-fit into the circular waveguide 306 section as well as into the feed 302 section to hermetically seal the probe 300 and to isolate the probe 300 from the flow 108. In an embodiment, the rod 308 of FIGS. 3(a) and 3(b) is press-fit into portions of the probe 300 to surround and insulate a center conductor that comprises a standard coaxial feed. The standard coaxial feed 309 is communicatively connected to a coaxial line port 312. In an embodiment, a matching flat bottom hole is machined into portions of the rod 308 to configure portions of the rod 308 for screwing into the feed 302 section structure.

Finally, in an embodiment, the antenna probe 300 is configured to be fitted with a commercial bored-through fitting comprising a ⅜" NPT (M) process connection suitable for high pressure applications. To install the transmitting and receiving antennas 115, 118, respectively, two ⅜" NPT (F) steel thread-o-lets are fitted on a flanged test section made out of standard 4-inch (~101 mm) steel pipe (~6.2 mm wall thickness) and PN16 flanges. The overall length of the antenna was ~7.0 cm and it was designed such that the open-ended aperture of the waveguide, such as waveguide 306 section, is offset from the inner pipe's wall surface by 2 mm.

Figure 4A:
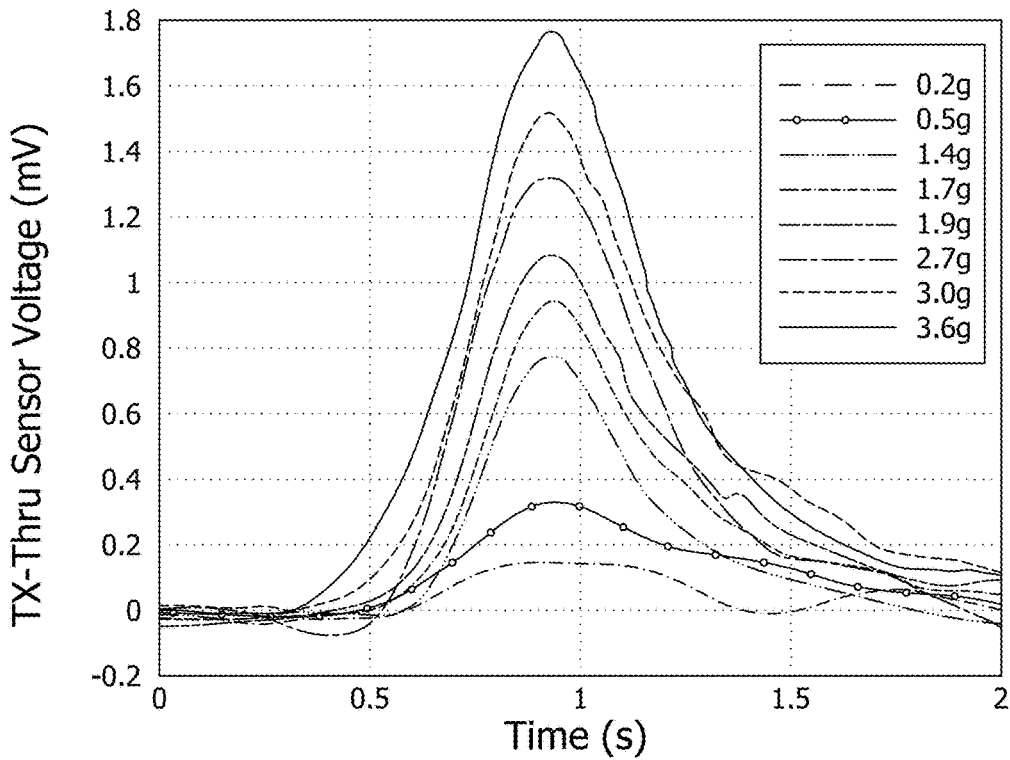
FIGS. 4(a) and 4(b) are exemplary graphs depicting measurement results according to an embodiment of the invention.
Figure 4B:
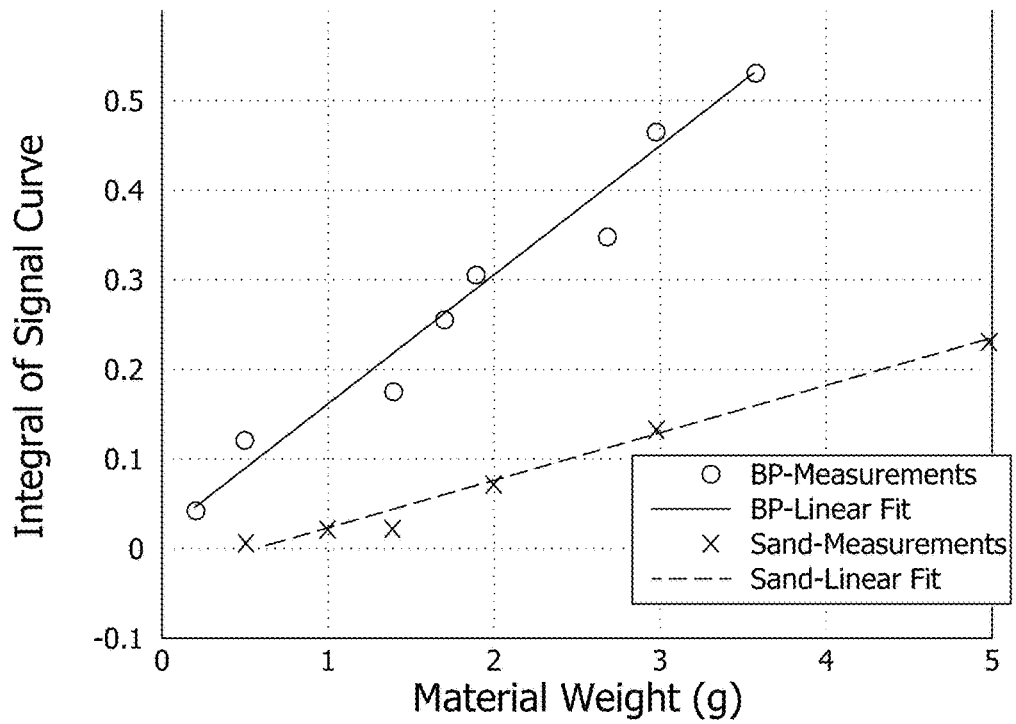

FIGS. 4(a) and 4(b) are exemplary graphs depicting measurement results. FIG. 4(a) depicts a transmitted-through response for various black powder sample weights, demonstrating real-time detection and assessment of black powder contaminants 107. In an embodiment, the detection apparatus 110 was used in a 3.6-m long experimental flow rig developed specifically for demonstration purposes. The experimental rig consisted of interconnected 4-inch ID (~101 mm) horizontal acrylic pipes and a 120-W DC fan as an air source. The flow created by the fan was rotational and had a maximum speed of 12 m/s (at the pipe's wall 103). While the air was flowing from the fan, black powder samples with known weight were deposited through a sealed material inlet into the flow 108 before the inline test section.

FIG. 4(b) depicts the correlation between the sample weight and the integral of the response curve for black powder and sand. It is evident that black powder flow rates as small as 0.2 g/s can be readily detected. To further demonstrate the measurement selectivity of the disclosed apparatus 110, the black powder experiment was repeated using sand samples. FIG. 4(b) illustrates a comparison between the detection response of black powder samples and the detection response of sand samples.

The design of the microwave detection circuitry subsystems can be changed without departing from the scope of this invention. For instance, coherent detectors (measuring phase and magnitude) can be used to detect the reflected and transmitted-through signals.

2. Microwave Imaging Apparatus and Method

Figure 5:
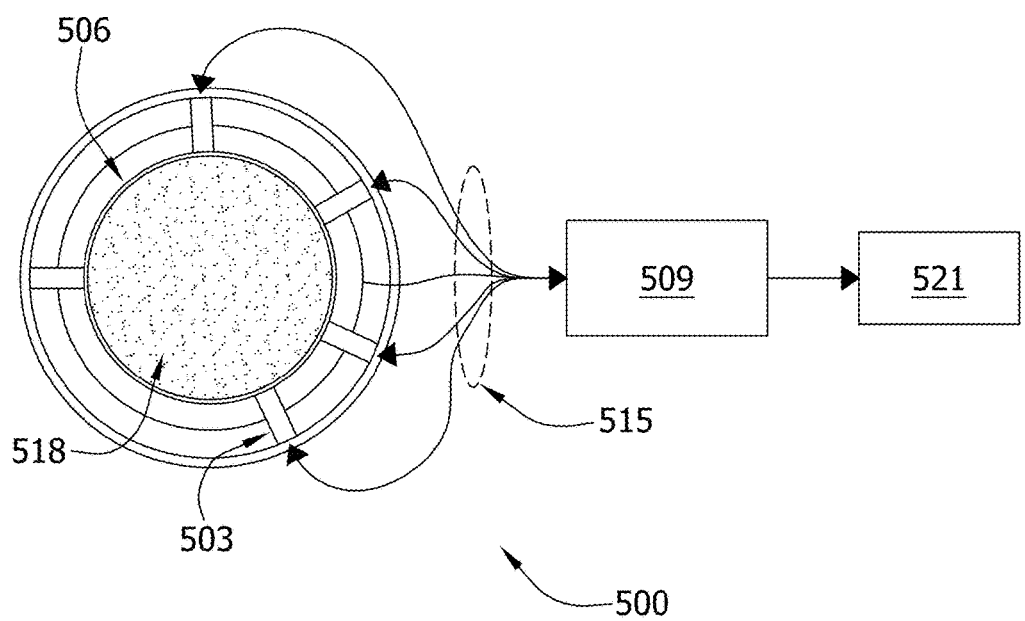
FIG. 5 depicts a microwave imaging system in accordance with an embodiment of the invention.

FIG. 5 depicts a microwave imaging system 500 according to another embodiment of the present invention. It is sometimes desired to visualize the distribution of black powder in a pipe 501. In addition to the microwave detection method described above, the imaging system 500 is capable of producing a visual rendering of black powder distribution within a cross section of the pipe 501. The microwave imaging system 500 assumes access to the inside of pipe 501. This can be accomplished by integrating an imaging array (e.g., see FIGS. 8(a)-(b), FIGS. 9(a)-(b)) within the pipe structure. The microwave imaging system 500 and its array of antennas are preferably non-perturbing to the flow in the pipeline and isolated from it. Microwave excitation is performed from localized points along the circumference and enclosing the test space.

The imaging system 500 disclosed in FIG. 5 comprises an N-channel microwave based imaging system based on a 2D imaging array working in the frequency range from 8-16 GHz. For instance, a uniform circular array embodies the 2D imaging array. Each antenna 503 is capable of transmitting and receiving a microwave signal in this frequency range. Hermetically-sealed wide band antennas are developed specifically for this purpose. In this particular embodiment, the array has an inner diameter of 4 inches, measured from a test section wall 506. To avoid spatial aliasing in the frequency range up to 16 GHz, a total of N=32 elements are used in one embodiment. As shown in FIG. 5, an N-channel transmitter/receiver module 509 connected to each antenna 503 by way of transmission lines 515 is configured to provide data describing detection results to display/storage components 521. In an embodiment, antenna 503 comprises transmitting antenna 115 and/or receiving antenna 118 as previously described. In another embodiment, the N-channel transmitter/receiver modules 509 are replaced by a single module (i.e., vector network analyzer) and a fast 1-to-32 microwave switch. As with the detection system, the array construction has means to withstand high pressures, providing for the detection of black powder contaminants 518.

Figure 6:
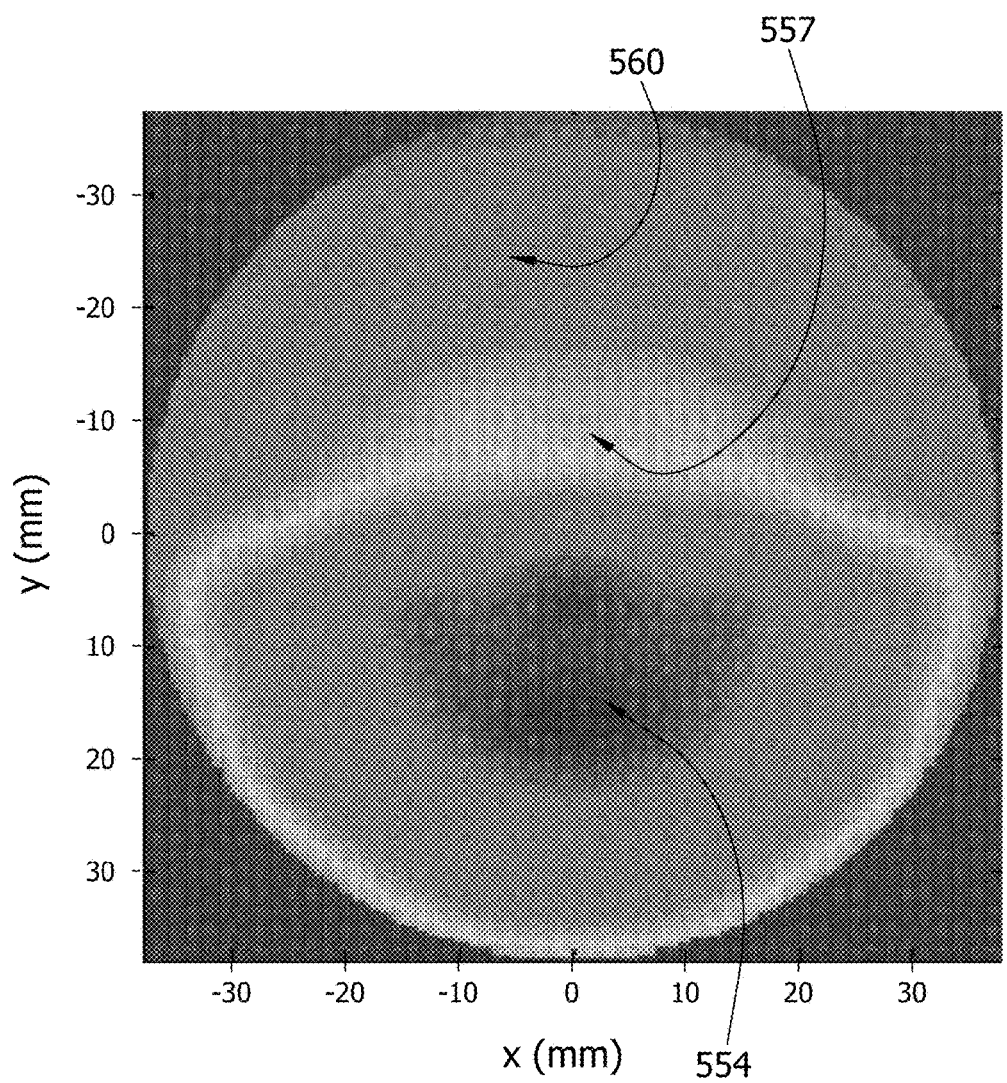
FIG. 6 depicts exemplary microwave imaging of black powder sediment illustrating an obtained image representing black powder distribution.

FIG. 6 depicts exemplary results obtained from the microwave imaging of black powder sediment illustrating an obtained image representing black powder distribution. With switched excitation/reception, the system described in FIG. 5, for example, is configured to facilitate robust monostatic measurements. In an embodiment, after cycling over each antenna 503, the detected signals (phase and magnitude) are processed to construct an image for the pipe cross section. In an embodiment, the image is representative of the gas flow mixture in the pipe 501 as a function of $V_T$ and $V_S$.

Additionally or alternatively, various well-established imaging algorithms are used for the purpose of constructing the pipe cross section image. In one non-limiting example, a synthetic focusing algorithm is utilized and implemented to produce an image for an irradiated medium. To illustrate this concept, a microwave imaging algorithm based on a bi-focusing operator was simulated to produce an actual distribution for black powder sentiment in a 3 inch pipe. In another embodiment, an image (illustrated by FIG. 6) is obtained for black powder sentiment in a 3 inch pipe, providing an image of a first detection region 554 that illustrates a greater presence of black powder sentiment in relation to a second detection region 557. In yet another embodiment, second detection region 557 illustrates a greater presence of black powder sentiment in relation to a third detection region 560.

Figure 7:
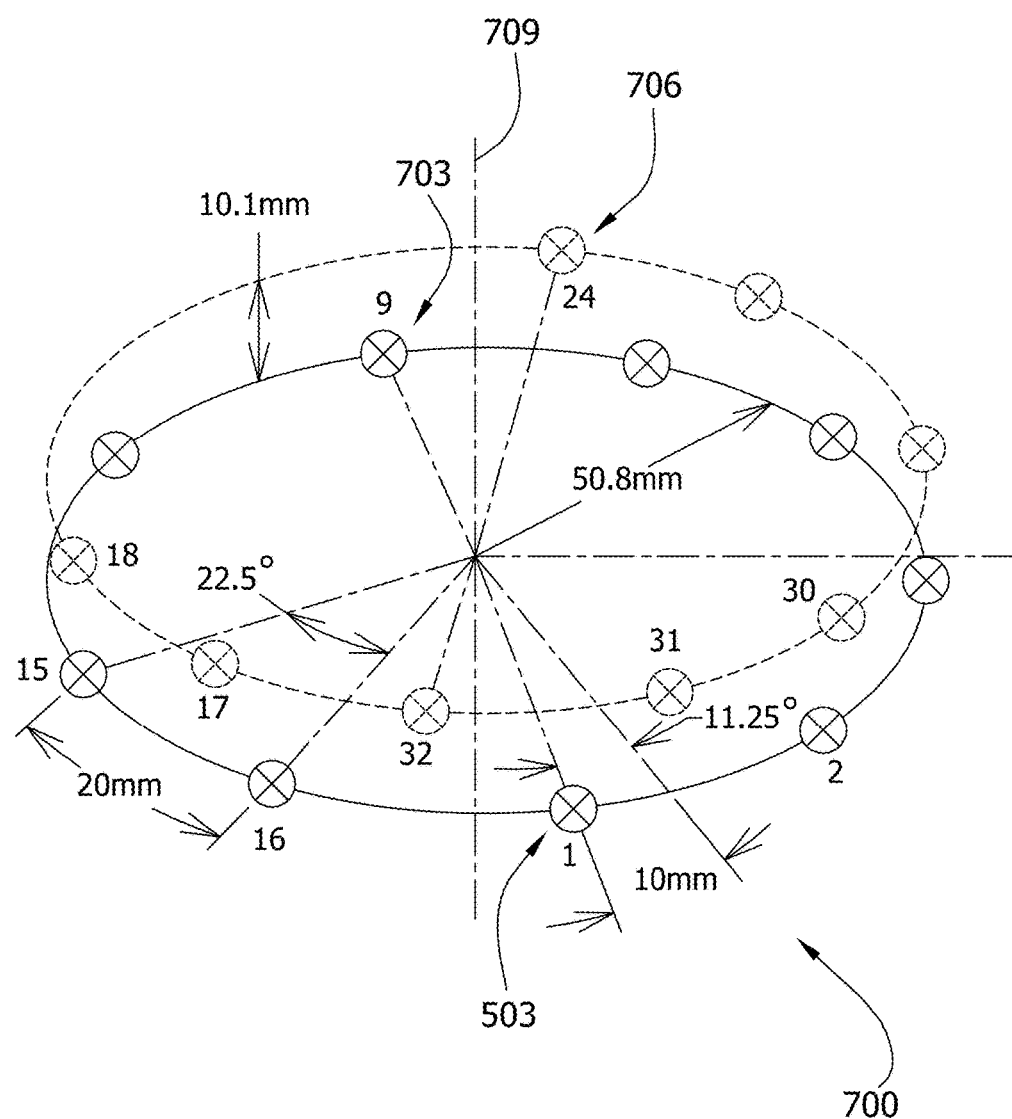
FIG. 7 depicts an array construction of a microwave imaging system in accordance with one embodiment of the invention.

FIG. 7 depicts array construction of a microwave imaging system 700 of the type shown in FIG. 5 in accordance with one embodiment of the invention. The imaging system 700 depicted by FIG. 7 is comprised of one or more antenna arrays that further comprise a hermetically sealed waveguide array. For example, the waveguide array includes 32 staggered rectangular waveguide elements integrated within the pipe structure. The imaging system 700 is designed to provide efficient means to withstand high gas pressures. The designed array in this embodiment comprises a circular array of 32 antennas. In an embodiment, the designed array comprises a first antenna (e.g., antenna 503) located in a first array, a second antenna 703 located in the first array and across the pipe from the antenna 503 for receiving the transmitted microwave signal through the fluid contained within the section of the pipe, and a third antenna 706 located downstream of the second antenna 703 for receiving the transmitted microwave signal through the fluid contained within the section of the pipe, as described herein.

In an embodiment, each antenna (e.g., antenna 503, second antenna 703, or third antenna 706) comprises a rectangular waveguide. In another embodiment, each rectangular waveguide has similar dimensions (width=0.5305 inch and height=0.2386 inch in one non-limiting example) filled with a fluorocarbon solid to isolate the element from the process, as previously described. The waveguide antennas 503, 703, 706 are configured specifically to provide for $TM_z$ test section illumination (i.e., illumination of the electric field along the pipe axis 709). Each array's antennas, such as antennas 503, 703, 706, are arranged into a concentric and identical circular array. For instance, each array of FIG. 7 comprises 16 waveguide elements interspaced center to center by a 20 mm arc. FIG. 7 illustrates the arrays by a first concentric circular array including antenna 503 and second antenna 703 and labeled 1, 2, 9, 15, and 16, respectively and a second, concentric, and identical circular array including antennas such as third antenna 706 labeled 17, 18, 24, 30, 31, and 32, respectively. In an embodiment, each concentric circular array is staggered by a uniform offset measurement. Additionally or alternatively, the circular arrays are interspaced by a uniform offset measurement along the pipe axis of 10.1 mm between each antenna (slightly larger than a quarter wavelength at 10 GHz). Additionally or alternatively, the concentric circular arrays are staggered by a uniform offset measurement of 11.25 degrees, as shown by FIG. 7.

Figure 8A:
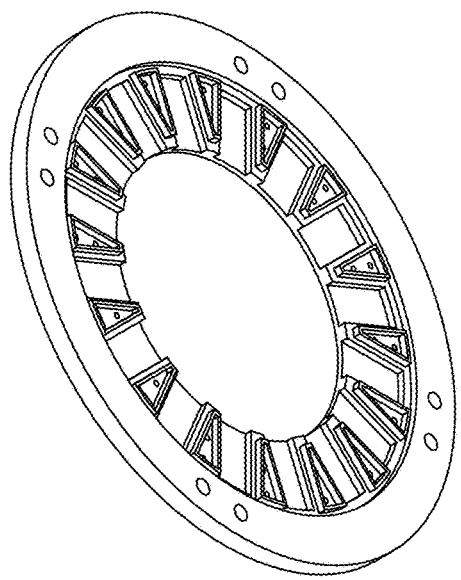
FIGS. 8(a) and 8(b) depict perspective and front views of part of an in-line array for use in a pipe in accordance with an embodiment of the invention.
Figure 8B:
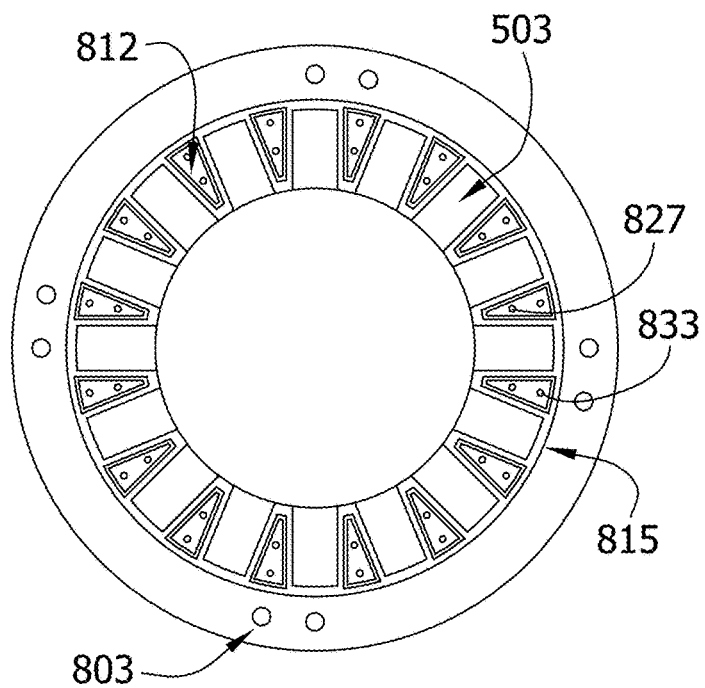
Figure 9A:
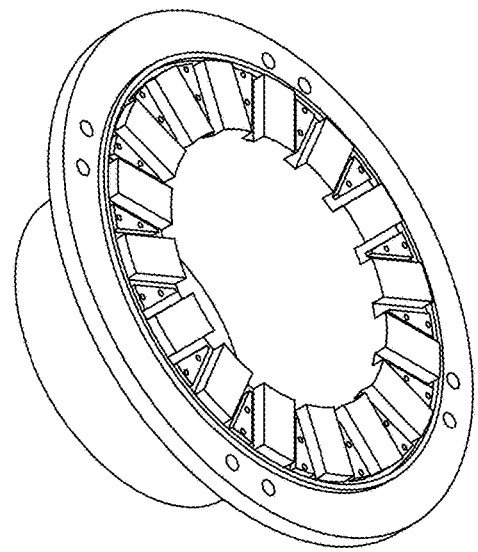
FIGS. 9(a) and 9(b) depict perspective and front views of another part of the in-line array for use with the part of FIGS. 8(a) and 8(b).
Figure 9B:
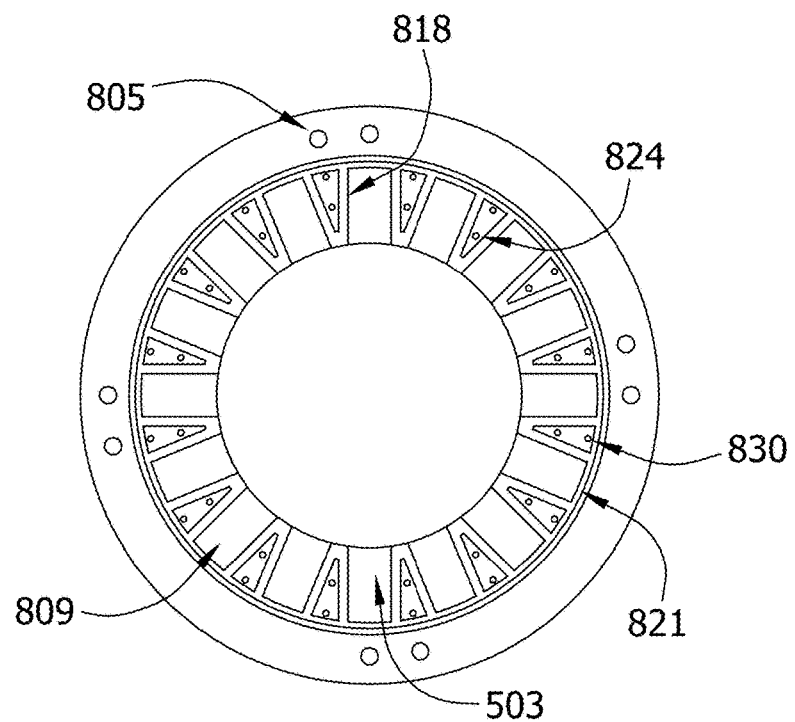
Figure 10A:
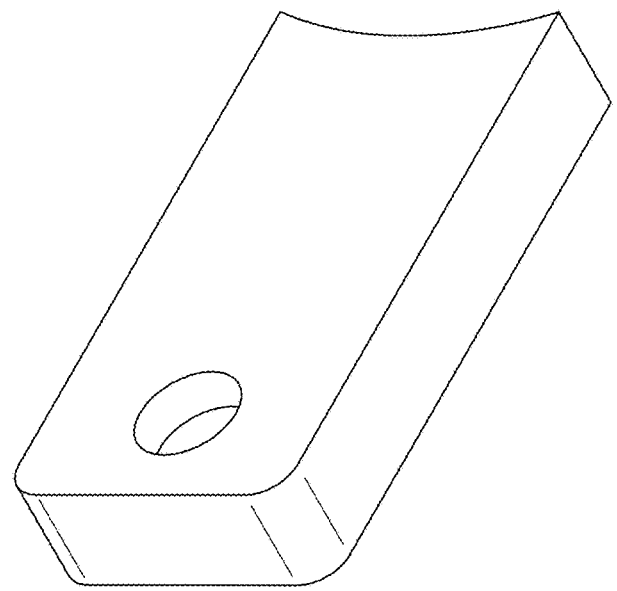
FIGS. 10(a) and 10(b) depict perspective and front views of an insert for use with the in-line array parts of FIGS. 8(a) and 8(b) and FIGS. 9(a) and 9(b).
Figure 10B:
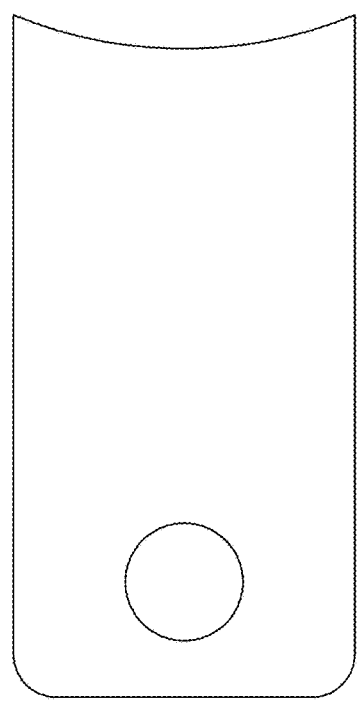

FIGS. 8(a)-(b), FIGS. 9(a)-(b), and FIGS. 10(a)-(b) depict perspective and front views of array parts comprising a center part (FIGS. 8(a) and 8(b)), a cover part (FIGS. 9(a) and 9(b)), and a filling (FIGS. 10(a) and 10(b)) in accordance with an embodiment of the invention. In an embodiment, each antenna (e.g., antenna 503, second antenna 703, or third antenna 706 as previously described) comprises a waveguide as described herein. For example, each antenna comprises a waveguide that is fed by a coaxial feed with TEM-to-$TE_{10}$ transition designed specifically to operate in the range from 8-16 GHz. The array parts are built on, for example, a custom made four inch pipe section. In an embodiment, a center part, such as shown in FIGS. 8(a) and 8(b), mates with a cover part, such as shown in FIGS. 9(b)

and 9(b), to form a circular array of uniformly spaced rectangular waveguides. In the illustrated embodiment, fluorocarbon solid inserts, as shown in FIGS. 10(a) and 10(b), fill the waveguides. It is to be understood that multiple arrays (e.g., as shown in FIG. 7) can be constructed by arranging center sections back to back with associated cover sections. In this embodiment, a gasket is preferably arranged in-between the center sections. In another embodiment, the array parts further comprise two cover sections (FIGS. 9(b) and 9(b)) arranged back to back with associated center sections. To reduce the cost of manufacturing, two identical center sections and covers are manufactured. For post-manufacturing alignment, M6 clearance holes 803 and M6 threads 805 are machined on a seven inch OD circle on each cover. Each M6 clearance hole 803 is offset from the threaded hole 805 by 11.25 degrees, in an embodiment. Aligned M6 clearance holes are machined into the center sections, in yet another embodiment.

With further reference to FIGS. 8(a)-(b), FIGS. 9(a)-(b), and FIGS. 10(a)-(b), each antenna further comprising a waveguide is machined into the center part such that the back, bottom, and two side walls of the waveguide are completely embedded in the center part. The cover part provides the top waveguide wall once the array is assembled. A coaxial feed is inserted through a feed hole 809 from the back of the cover part into the fluorocarbon solid insert or filling of the waveguide. In an embodiment, various design specifications provide for an array structure capable of withstanding high pressures. The center sections are constructed with radial 812 and circumferential 815 tongues as shown in FIGS. 8(a) and 8(b). In another embodiment, the cover sections are constructed with radial 818 and circumferential 821 grooves as shown in FIGS. 9(a) and 9(b), resulting in a tongue-groove assembly allowing for the electromagnetic isolation of array elements (such as antenna 503 comprising a waveguide, for example) from each other as well as making the array structure withstand high pressure and avoid any fluid leakage. If needed, sealants can be used in the grooves without impairing the functionality of the array.

Still referencing FIGS. 8(a)-(b), FIGS. 9(a)-(b), and FIGS. 10(a)-(b), each pair of cover and center parts are assembled together by inserting M3.5 and M2.5 screws through M2.5 hole 824 and M2.5 thread 827, as well as M3.5 hole 830 and M3.5 thread 833. This procedure results in two identical cover-center assemblies. These two assemblies are placed such that the center section's flat faces are parallel. Then, M6 screws should be inserted through the clearance holes 803 of one cover-center assembly and screwed into an aligned M6 thread 805 in the second cover-center assembly.

Figure 11:
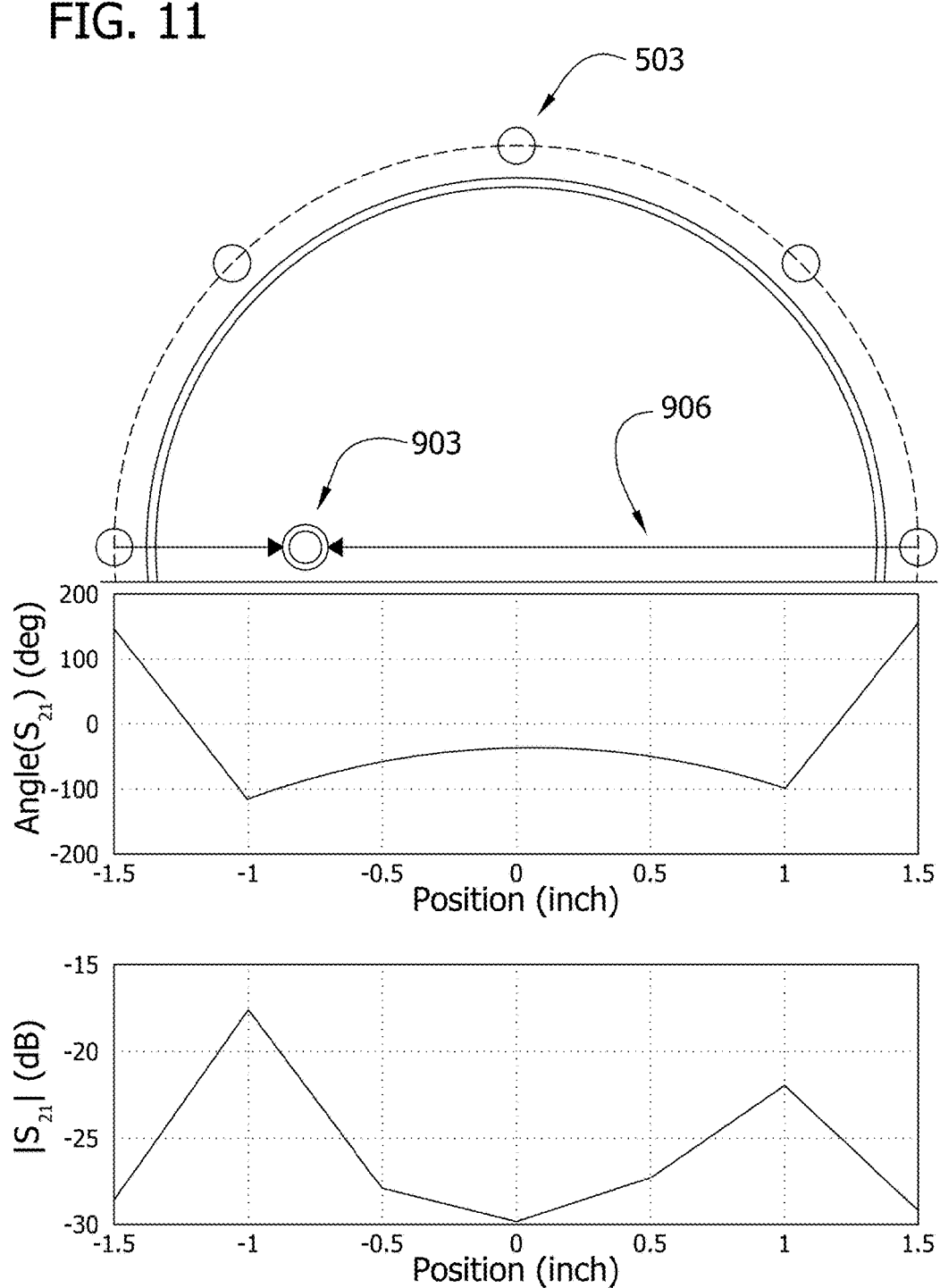
FIG. 11 is an exemplary graph depicting an array-produced response due to target movement in the cross section of the pipe.

FIG. 11 is a graph depicting an exemplary array-produced response due to target movement in the cross section of the pipe. Due to the unique tongue-groove assembly surrounding each antenna comprising an array element as described above, the disclosed array provides high isolation between the array elements. The symmetry in construction results in symmetric response. The sensitivity of the system to a target 903 within the pipe cross section is demonstrated in FIG. 11, which illustrates a typical measured response as a target 903 traverses the pipe cross section along a line 906 connecting any two elements. As demonstrated in FIG. 11, the phase and magnitude response as a function of the position of target 903 is indicative of the sensitivity of the apparatus as an imaging system.

Placing a cylindrical nylon rod within the imaging array and displaced towards one of side of the pipe highlights the capabilities of the disclosed imaging system. To highlight the capability of the disclosed imaging system for detecting and localizing relatively small targets, a cylindrical nylon rod comprised of 0.78-inch OD was placed coaxially within the imaging array while displaced towards one of side of the pipe. A total signal bandwidth of 8 GHz (8-16) was used to produce an image for the target considered in this demonstration. The disclosed system can produce clear indication for the presence of the target (i.e., the rod) as well as render a clear image from which the location of the target can be readily estimated.

Figure 12:
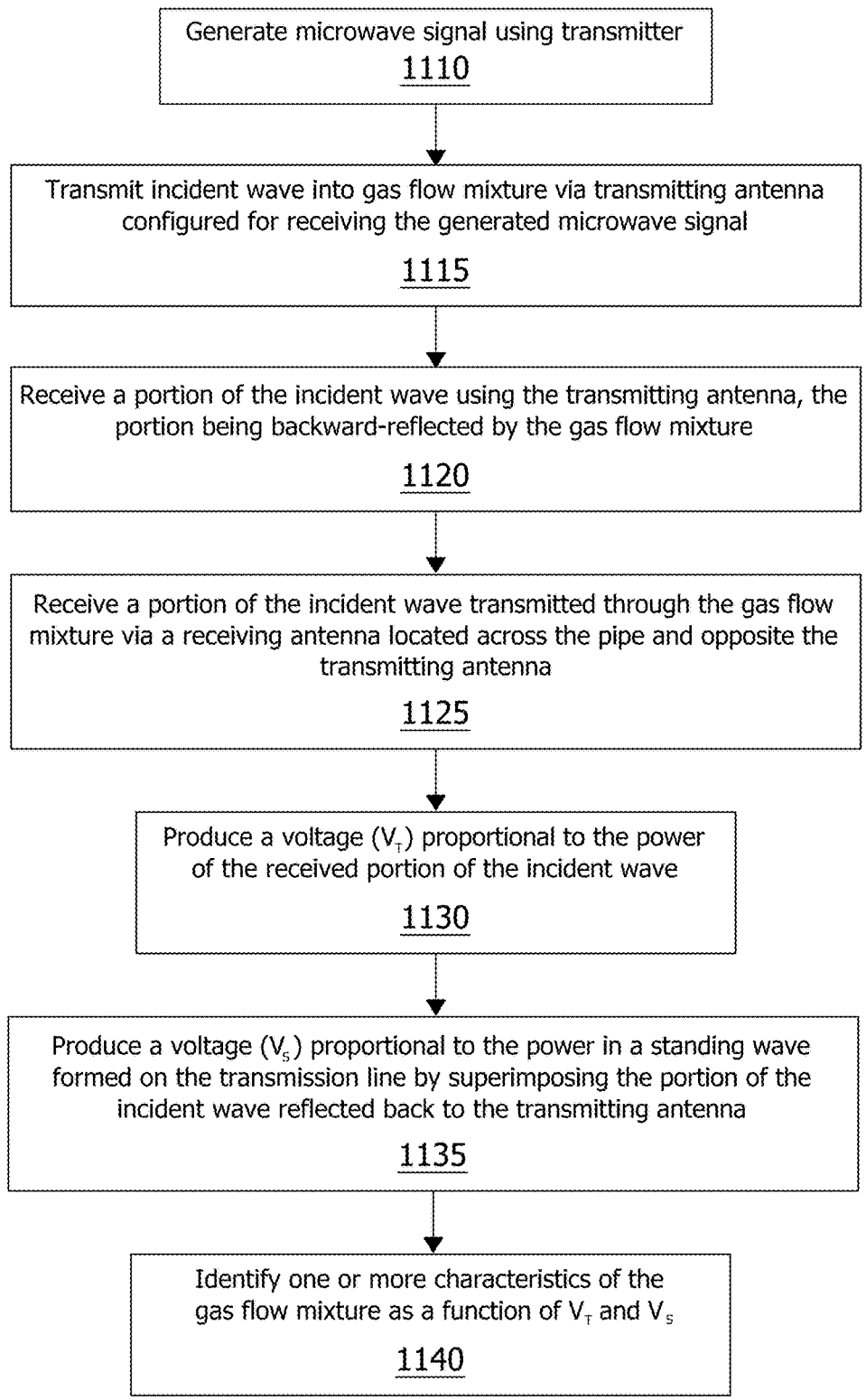
FIG. 12 is an exemplary flow diagram depicting a method of microwave detection and imaging in accordance with one embodiment of the invention.

FIG. 12 depicts a method for detecting components within a pressurized gas flow mixture, in accordance with an embodiment of the invention. The process begins at 1110, comprising generating, by a transmitter, a microwave signal. Step 1115 comprises transmitting, via a transmitting antenna configured for receiving the microwave signal, an incident wave into a gas flow mixture contained within a pipe, said transmitting antenna being coupled to the transmitter via a transmission line. Next, at 1120, the process comprises receiving, via the transmitting antenna, at least a portion of the incident wave reflected back to the transmitting antenna by the gas flow mixture.

With further reference to FIG. 12, the process continues at 1125 with receiving, via a receiving antenna, at least a portion of the incident wave transmitted through the gas flow mixture, said receiving antenna being located substantially opposite the transmitting antenna across the pipe. Next, at 1130, the process comprises producing a voltage ($V_T$) proportional to the power of the received portion of the incident wave transmitted through the gas flow mixture. The process further comprises producing a voltage ($V_S$) proportional to the power in a standing wave formed on the transmission line by superimposing the portion of the incident wave reflected back to the transmitting antenna by the gas flow mixture on the microwave signal, as illustrated by step 1135. Finally, the process concludes at 1140 with; identifying one or more characteristics of the gas flow mixture as a function of $V_T$ and $V_S$.

Still referring to FIG. 12, it is to be understood that the presence of black powder, even at a relatively small volume within the process flow, is manifested with considerable variations in the microwave transmission properties of the process flow rendering high overall detection sensitivity. Therefore, it is to be understood that the method described in FIG. 11 allows for the identification of one or more characteristics of the gas flow mixture that in turn describe considerable variations in the microwave transmission properties of the pressurized gas flow mixture, resulting in high overall detection sensitivity.

Advantageously, both the detection and imaging systems can be equipped with means to measure the mass flow rate. In the detection system, an addition of one or more probes (such as an antenna 503, a second antenna 703, or a third antenna 706, each of the antennas further comprising a waveguide in an embodiment, as described herein) displaced along the axis of the pipe provides such a means. In the imaging system, since there are two arrays along the pipe axes, the relative measurements between these arrays can be readily used to measure the flow rate, and to construct an image that comprises the mass flow rate measurement.

Moreover, the imaging system is a more general embodiment of the detection system. In an embodiment, a subset of the imaging system can be used to perform the detection and quantification of black powder.

Both the detection and imaging system are configured to utilize conventional phase and/or magnitude modulation schemes as well common time- and/or frequency multiplexing techniques of the transmitted and/or received signals to enhance sensitivity, resolution, and/or reduce system complexity.

Embodiments of the aspects of the invention may be implemented with processor-executable instructions. The processor-executable instructions may be organized into one or more processor-executable components or modules on a tangible processor readable storage medium. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention is not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and process without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the aspects of the invention as set forth in the claims that follow. The specification and drawings are accordingly to be regarded in an illustrative rather than restrictive sense.

What is claimed is:

1. An apparatus for characterizing multiphase flow in a pipe transporting a fluid under pressure, comprising:
   a transmitter for generating a microwave signal;
   a first antenna coupled to the transmitter for transmitting the microwave signal into the fluid contained within a section of the pipe and for receiving a reflected microwave signal reflected from the fluid contained within the section of the pipe;
   a first diode detector in communication with the first antenna via a transmission line, said first diode detector configured for detecting a standing wave on the transmission line, said standing wave comprising the transmitted microwave signal and the reflected microwave signal, said first diode detector producing a first voltage representative of the standing wave;
   a second antenna located across the pipe from the first antenna for receiving the transmitted microwave signal through the fluid contained within the section of the pipe;
   a second diode detector in communication with the second antenna for receiving the transmitted microwave signal from the second antenna and for producing a second voltage representative thereof;
   a pre-amplifier/filter for pre-processing the received first and second voltage signals;
   an analog-to-digital converter for converting the pre-processed received voltage signals from analog to digital; and
   a monitoring processor receiving and responsive to the converted voltage signals for identifying characteristics of the flow as a function thereof.

2. The apparatus of claim 1, wherein the processor is configured for correlating a concentration of a contaminant within multi-phase flow based on phase angle and amplitude of the standing wave.

3. The apparatus of claim 1, wherein the processor is configured for correlating a concentration of a contaminant within multi-phase flow based on phase angle and amplitude of the transmitted signal through the flow.

4. The apparatus of claim 1, further comprising a third antenna located downstream of the second antenna for receiving the transmitted microwave signal through the fluid contained within the section of the pipe, and wherein the processor is configured for characterizing multi-phase flow within the pipe based on a time domain shift in the transmitted microwave signals from the second and third antennas.

5. The apparatus of claim 4, wherein the first, second, and third antennas are hermetically sealed and isolated from the process fluid.

6. The apparatus of claim 4, wherein the first, second, and third antennas comprise circular waveguides.

7. The apparatus of claim 6, wherein the circular waveguides are integrally formed in a wall of the pipe.

8. The apparatus of claim 4, wherein the first, second, and third antennas comprise rectangular waveguides.

9. The apparatus of claim 4, wherein the first and second antennas are arranged in a first array of staggered elements.

10. The apparatus of claim 9, wherein the first array is integrally formed in a wall of the pipe.

11. The apparatus of claim 9, wherein the third antenna is arranged in a second array.

12. The apparatus of claim 11, wherein the second array is integrally formed in a wall of the pipe.

13. The apparatus of claim 12, wherein the first array and the second array are staggered by a uniform offset measurement comprising at least one of:
    a predetermined measurement between each array along the pipe axis; and,
    a predetermined measurement between the first antenna arranged in the first array and the third antenna arranged in the second array comprising at least one of:
        a distance greater than one quarter wavelength at a microwave frequency;
        a predetermined angular measurement; and,
        a predetermined linear measurement.

14. The apparatus of claim 9, wherein the processor is configured for generating an image representative of the gas flow mixture in the pipe as a function of phase and magnitude of the transmitted through signals or reflected signals, or a combination of both provided by the first array.

15. A method for detecting components within a pressurized gas flow mixture, comprising:
    generating, by a transmitter, a microwave signal;
    transmitting, via a transmitting antenna configured for receiving the microwave signal, an incident wave into a gas flow mixture contained within a pipe, said transmitting antenna being coupled to the transmitter via a transmission line;
    receiving, via the transmitting antenna, at least a portion of the incident wave reflected back to the transmitting antenna by the gas flow mixture;
    receiving, via a receiving antenna, at least a portion of the incident wave transmitted through the gas flow mixture, said receiving antenna being located substantially opposite the transmitting antenna across the pipe;
    producing, by a first diode detector, a voltage ($V_T$) proportional to the power of the received portion of the incident wave transmitted through the gas flow mixture;
    producing, by a second diode detector, a voltage ($V_S$) proportional to the power in a standing wave formed on the transmission line by superimposing the portion of the incident wave reflected back to the transmitting antenna by the gas flow mixture on the microwave signal; and
    identifying, by a monitoring processor, one or more characteristics of the gas flow mixture as a function of $V_T$ and $V_S$.

16. The method of claim 15, wherein the identified one or more characteristics of the gas flow mixture comprise variations in the microwave transmission properties of the pressurized gas flow mixture.

17. The method of claim 15, further comprising generating an image representative of the gas flow mixture in the pipe as a function of $V_T$ and $V_S$.

18. The method of claim 17 wherein the generated image further comprises a mass flow rate measurement.

19. The method of claim 18, further comprising:
    providing an array element configured for said transmitting an incident wave, said receiving at least a portion of the incident wave reflected back to the transmitting antenna, and said receiving at least a portion of the incident wave transmitted through the gas flow mixture;
    wherein the mass flow rate measurement is generated by relative measurements obtained by a first array element and a second array element.

20. The method of claim 19, further comprising quantifying a concentration of black powder based upon a dielectric contrast between the pressurized gas flow mixture and the components within the pressurized gas flow mixture.

* * * * *